(12) United States Patent
Daikoku et al.

(10) Patent No.: US 9,038,472 B2
(45) Date of Patent: May 26, 2015

(54) TESTING METHOD USING GUIDED WAVE

(75) Inventors: Koki Daikoku, Kanagawa (JP); Masato Yoshizaki, Kanagawa (JP); Shuichi Sato, Kanagawa (JP)

(73) Assignee: IHI Inspection and Instrumentation Co., Ltd., Tokyo (JP)

( * ) Notice: Subject to any disclaimer, the term of this patent is extended or adjusted under 35 U.S.C. 154(b) by 300 days.

(21) Appl. No.: 13/574,151

(22) PCT Filed: Feb. 12, 2010

(86) PCT No.: PCT/JP2010/052068
§ 371 (c)(1),
(2), (4) Date: Jul. 19, 2012

(87) PCT Pub. No.: WO2011/089733
PCT Pub. Date: Jul. 28, 2011

(65) Prior Publication Data
US 2012/0285247 A1    Nov. 15, 2012

(30) Foreign Application Priority Data

Jan. 21, 2010 (JP) ................................. 2010/010745

(51) Int. Cl.
*G01N 29/36* (2006.01)
*G01N 29/24* (2006.01)
*G01N 29/11* (2006.01)
*G01N 29/44* (2006.01)

(52) U.S. Cl.
CPC ............ *G01N 29/2412* (2013.01); *G01N 29/11* (2013.01); *G01N 29/44* (2013.01); *G01N 2291/0425* (2013.01); *G01N 2291/044* (2013.01); *G01N 2291/2634* (2013.01)

(58) Field of Classification Search
USPC .......................................... 73/599, 600, 622
See application file for complete search history.

(56) References Cited

U.S. PATENT DOCUMENTS

| 4,825,423 A | 4/1989 | Yamanaka |
| 7,234,355 B2 | 6/2007 | Dewangan et al. |

(Continued)

FOREIGN PATENT DOCUMENTS

| JP | 61-76953 A | 4/1986 |
| JP | 5-75267 B2 | 10/1993 |

(Continued)

OTHER PUBLICATIONS

Toyokazu Komatsu et al., "Sensitivity of guided wave for gradually increasing defects to the axial direction of pipes", 2009 Nendo Nenji Taikai Koen Ronbunshu, vol. 9./No. 1, The Japan Society of Mechanical Engineers, Sep. 12, 2009, 451-452 (with partial translation).

(Continued)

*Primary Examiner* — Laura Martin
*Assistant Examiner* — Rose M Miller
(74) *Attorney, Agent, or Firm* — Griffin & Szipl, P.C.

(57) ABSTRACT

A testing method using a guided wave generates a guided wave to propagate through a subject as a testing target in a longitudinal direction of the subject, detects a reflected wave of the guided wave and examines the subject on the basis of the reflected wave. The testing method includes the steps of (A) obtaining data for defect amount estimation beforehand indicating a relationship between a defect amount of the subject and a magnitude of a reflected wave, (B) generating a guided wave so as to propagate through the subject, and detecting a reflected wave of the guided wave, and (C) estimating a defect amount of the subject on the basis of the data for defect amount estimation obtained at (A) and the magnitude of the guided wave detected at (B).

4 Claims, 6 Drawing Sheets

(56) References Cited

U.S. PATENT DOCUMENTS 7,634,392 B2    12/2009  Kwun et al.
2004/0255678 A1* 12/2004 Nagashima et al. ............ 73/620
2009/0031813 A1  2/2009  Miki et al.

FOREIGN PATENT DOCUMENTS

| JP | 8-30698 B2 | 3/1996 |
| JP | 2006-170754 A | 6/2006 |
| JP | 2008-292385 A | 12/2008 |
| JP | 2009-36516 A | 2/2009 |

OTHER PUBLICATIONS

Search Report issued in corresponding application PCT/JP2010/052068, completed Mar. 3, 2010 and mailed Mar. 16, 2010.

Search Report issued in related application PCT/JP2010/052070, completed Feb. 25, 2010 and mailed Mar. 9, 2010.

Office Action issued in co-pending related U.S. Appl. No. 13/574,187 on Sep. 12, 2014.

* cited by examiner

TESTING METHOD USING GUIDED WAVE

This is a National Phase Application in the United States of International Patent Application No. PCT/JP2010/052068 filed Feb. 12, 2010, which claims priority on Japanese Patent Application No. 010745/2010, filed Jan. 21, 2010. The entire disclosures of the above patent applications are hereby incorporated by reference.

TECHNICAL FIELD

The present invention relates to a testing method for a subject to be tested (hereinafter simply called a subject) in the shape of a tube or a rod. More particularly the present invention relates to a testing method including the steps of: generating a guided wave that is a sound wave to propagate through a subject as a testing target in the longitudinal direction of the subject; detecting a reflected wave of the guided wave; and examining the subject on the basis of the reflected wave. The guided wave typically has a frequency from 1 kHz to several hundreds kHz (in one example, 32 kHz, 64 kHz or 128 kHz).

BACKGROUND ART

A guided wave can be generated by the passage of AC current through a coil wound around a subject, for example. That is, AC current flowing through a coil wound around a subject generates AC magnetic field. A magnetic force from this AC magnetic field can be used to vibrate the subject, whereby a guided wave as a kind of sound waves can be generated. The thus generated oscillation wave propagates through the subject along the longitudinal direction thereof.

A reflected wave of the guided wave is detected, whereby the soundness of the subject can be tested. A guided wave is reflected as a reflected wave at a discontinuous part of the subject or at a part of a change in cross-sectional area of the subject in the circumferential direction. This reflected wave is detected at an oscillation position of the guided wave, whereby the soundness of the subject is tested. The soundness of the subject is tested about the presence or absence of a defect part such as a flaw, corrosion or the like of the subject.

Examples of the guided wave include an L-mode (Longitudinal mode) guided wave and a T-mode (Torsional mode) guided wave. The L-mode guided wave propagates through a subject while vibrating in the propagation direction, and the T-mode guided wave propagates through a subject while torsionally vibrating in the subject.

Such a guided wave suffers less attenuation than a sound wave used for general sound wave testing, and therefore enables testing of a subject for the soundness over a wide range of the subject. A sound wave used for general sound wave testing has a high frequency of 5 MHz and a small wavelength of 0.6 mm, for example, and for this reason, is likely to attenuate. On the other hand, the above-stated guided wave has a small frequency of 32 kHz and a large wavelength of 100 mm, for example, and for this reason, suffers less attenuation.

The following Patent Document 1 is available, for example, as a prior art document of the present application.

PRIOR ART DOCUMENT

Patent Document

Patent Document 1: Japanese Patent application Publication No. 2009-36516

SUMMARY OF THE INVENTION

Problem to be Solved by the Invention

Conventionally, a technique to locate the defect part is available. However there is no technique for precise measurement of the defect amount such as measurement of the cross-sectional area and the width of the defect. The position of a defect part can be found by detecting a reflected wave of a guided wave. Such a position can be found based on an elapsed time from oscillation timing of a guided wave to detection timing of a reflected wave thereof. On the other hand, conventionally there is no technique for precise measurement of the defect amount.

In view of this, it is an object of the present invention to provide a testing method using a guided wave capable of finding precisely not only the position of a defect part of a subject but also the defect amount.

Means for Solving the Problem

In order to fulfill such an object, a present invention provides a testing method using a guided wave, of generating a guided wave to propagate through a subject as a testing target in a longitudinal direction of the subject, detecting a reflected wave of the guided wave and examining the subject on the basis of the reflected wave. In this method, (A) data for defect amount estimation is obtained beforehand, the data for defect amount estimation indicating a relationship between a defect amount of the subject and amplitude of the reflected wave or the duration of the reflected wave, (B) a guided wave is generated so as to propagate through the subject, and a reflected wave of the guided wave is detected, and (C) on the basis of the data for defect amount estimation obtained at (A) and amplitude of the reflected wave or the duration of the reflected wave detected at (B), a defect amount of the subject is estimated.

According to a preferred embodiment of the present invention, the defect amount is a cross-sectional area of a defect part taken along a plane orthogonal to an axial direction of the subject, and the data for defect amount estimation is data for cross-sectional area estimation indicating a relationship between the cross-sectional area of the defect part and the amplitude of the reflected wave.

The defect amount may be a width of a defect part in an axial direction of the subject, and the data for defect amount estimation may be data for defect width estimation indicating a relationship between the width of the defect part and the duration of the reflected wave.

According to another embodiment of the present invention, (D) three-variables correspondence data is obtained beforehand, the three-variables correspondence data indicating a relationship among amplitude of a reflected wave, a width of a defect part and a cross-sectional area of the defect part, and (E) on the basis of the width of the defect part estimated at (C), the amplitude of the guided wave detected at (B) and the three-variables correspondence data, a cross-sectional area of the defect part is estimated.

Preferably, in (A), a subject for testing of a same type as the subject as a testing target is prepared, a guided wave is propagated through the subject for testing and a reflected wave thereof at a defect part is detected, whereby on the basis of a defect amount of each of a plurality of defect parts and the reflected waves corresponding to the plurality of defect parts, the data for defect amount estimation is obtained.

Preferably, in (D), a subject for testing of a same type as the subject as a testing target is prepared, a guided wave is propagated through the subject for testing and a reflected wave thereof at a defect part is detected, whereby on the basis of a width and a cross-sectional area of each of a plurality of defect parts and amplitude of the reflected waves corresponding to the plurality of defect parts, the three-variables correspondence data is obtained.

Advantages of the Invention

According to the aforementioned present invention, (A) data for defect amount estimation is obtained beforehand, the data for defect amount estimation indicating a relationship between a defect amount of the subject and amplitude of the reflected wave or duration of the reflected wave, (B) a guided wave is generated so as to propagate through the subject, and a reflected wave of the guided wave is detected, and (C) on the basis of the data for defect amount estimation obtained at (A) and amplitude of the reflected wave or duration of the reflected wave detected at (B), a defect amount of the subject is estimated. Therefore, a defect amount of the subject can be found precisely.

EMBODIMENTS OF THE INVENTION

Figure 1:
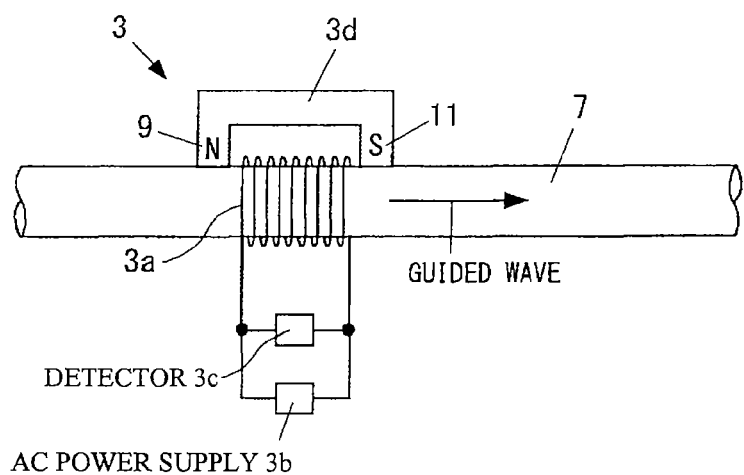
FIG. 1 illustrates an exemplary configuration of a testing device that can be used for a testing method using a guided wave according to an embodiment of the present invention.

The following describes preferred embodiments of the present invention, with reference to the drawings. In the drawings, the same reference numerals are assigned to common elements, and the duplicated descriptions are omitted.

Embodiment 1

FIG. 1 illustrates an exemplary configuration of a testing device 3 that can be used for a testing method using a guided wave according to Embodiment 1 of the present invention. The testing device 3 of FIG. 1 is configured to generate an L-mode guided wave so as to propagate through a subject 7 as a testing target made of metal, glass, resin or the like in the longitudinal direction, detect a reflected wave of the guided wave and examine the subject 7 based on the reflected wave. The testing device 3 includes a coil $3a$, a magnet $3d$, an AC power supply $3b$ and a detector $3c$.

The subject 7 is tubular or rod-shaped. For instance, the tubular subject 7 may be piping through which fluid flows, and the rod-shaped subject 7 may be a ground anchor, an anchor bolt or a reinforcing iron bar.

The coil $3a$ is wound around the subject 7. The magnet $3d$ is disposed so that the north pole 9 thereof is located on one side of the coil $3a$ in the axial direction of the subject 7 and the south pole 11 thereof is located on the other side of the coil $3a$ and so that the coil $3a$ is sandwiched between the north pole 9 and the south pole 11. These north pole 9 and south pole 11 are fixed to an outer periphery face of the subject 7 with appropriate means so that these poles are pressed against toward the center axis of the subject 7. The detector $3c$ is connected to the coil $3a$ for detection of a voltage between both ends of the coil $3a$.

Arranging the coil $3a$, the magnet $3d$ and the detector $3c$ in this way, when AC current is passed through the coil $3a$ from the AC power supply $3b$, an L-mode guided wave is generated in the subject 7, and the guided wave propagates along the longitudinal direction of the subject 7. Such a propagating guided wave is reflected at a defect part such as a flaw or corrosion (wastage) of the subject 7 and returns to the coil $3a$ side by propagation. The detector $3c$ detects a voltage generated between both ends of the coil $3a$ as the reflected wave reaches the part of the subject 7 around which the coil $3a$ is wound.

Figure 2:
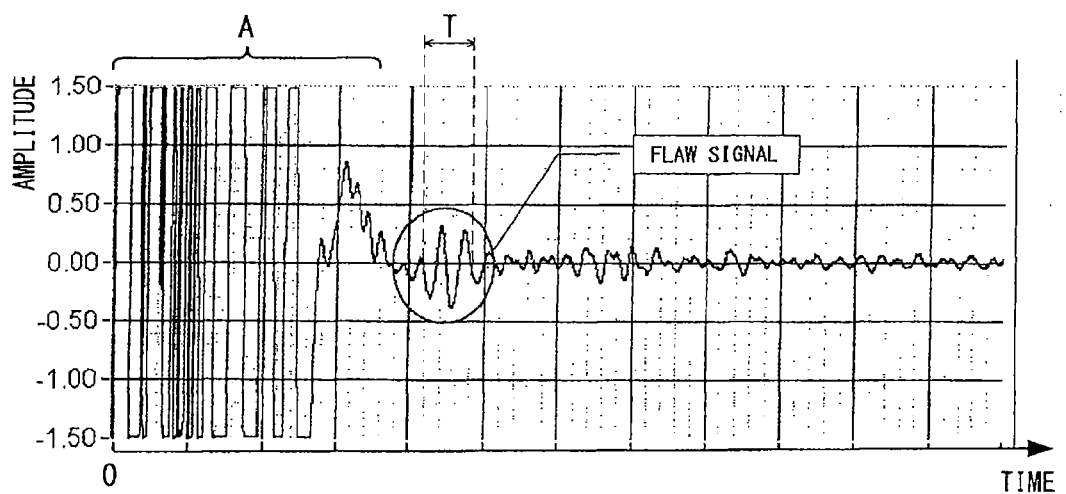
FIG. 2 illustrates a waveform of a reflected wave that the testing device of FIG. 1 detected.

FIG. 2 illustrates a waveform of the reflected wave that the detector $3c$ of the testing device 3 of FIG. 1 detected. In FIG. 2, the horizontal axis represents time (corresponding to a distance from the attachment position of the coil $3a$, $5a$ along the longitudinal direction of the subject 7). The vertical axis represents amplitude of a voltage (i.e., amplitude of the reflected wave) between both ends of the coil $3a$, $5a$. In FIG. 2, the waveform shows that the amplitude of the reflected wave is larger at the part surrounded with the circle (flaw signal) than at other parts, meaning that there is a defect such as a flaw or corrosion at a position of the subject 7 corresponding to this surrounded part. In FIG. 2, the waveform in the range A shows a voltage applied from AC power supplies $3b$, $5b$ at the time of the generation of the guided wave. The origin of the time in FIG. 2 corresponds to the time when the guided wave is generated.

Figure 3:
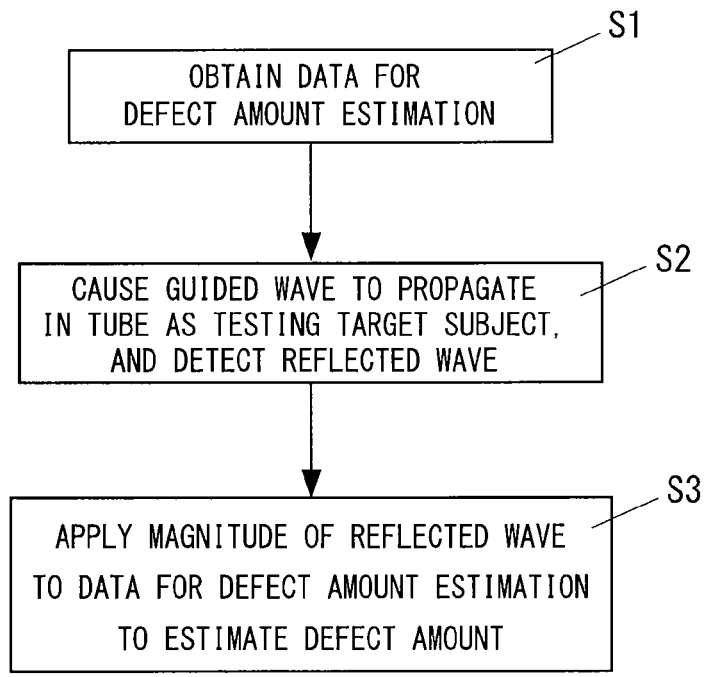
FIG. 3 is a flowchart illustrating a testing method using a guided wave according to Embodiment 1 of the present invention.

FIG. 3 is a flowchart illustrating a testing method using a guided wave according to Embodiment 1 of the present invention.

At Step S1, data for defect amount estimation is obtained beforehand, the data indicating a relationship between the defect amount of a subject and amplitude of the reflected wave or duration of the reflected wave. Preferably at Step S1 a subject 8 for testing of the same type as the subject 7 as a testing target is prepared, a guided wave is propagated through the subject 8 for testing and a reflected wave from a defect part is detected, whereby the data for defect amount estimation is obtained based on the defect amounts at a plurality of defect parts and the reflected waves corresponding to the plurality of defect parts.

At Step S2, a guided wave to propagate through the subject 7 is generated, and a reflected wave of this guided wave is detected. More specifically, this step is as follows. Firstly, the testing device 3 is attached at an attachment position of the subject 7 as a testing target. That is, at the attachment position located at a predetermined part in the axial direction of the subject 7, the coil 3a is wound around an outer periphery face of the subject 7 about an axis of the subject 7. Then the magnet 3d, the AC power supply 3b and the testing device 3 are arranged as stated above. Next, a switch provided at a wiring connecting the AC power supply 3b and the coil 3a is turned on with appropriate means, whereby AC current is passed through the coil 3a. As a result an L-mode guided wave is generated, and this guided wave propagates along the longitudinal direction of the subject 7 as a testing target. A reflected wave of such an L-mode guided wave propagating through the subject 7 is detected by the detector 3c. The detector 3c acquires the waveform of the reflected wave as illustrated in FIG. 2, for example.

Herein, preferably at Step S2, the time duration for which the switch is being turned on is controlled so that a guided wave of a desired short length (e.g., about two to three wavelengths) is generated for propagation. After such time duration for which the switch is being turned on, then the switch is turned off so as not to pass current from the AC power supply 3b to the coil 3a.

At Step S3, based on the data for defect amount estimation obtained at Step S1 and the amplitude or duration of the reflected wave detected at Step S2, the defect amount of the subject 7 as a testing target is estimated. That is, the amplitude or duration of the detected reflected wave is applied to the data for defect amount estimation (e.g., a proportional relationship illustrated later in FIG. 6 or FIG. 8), whereby the defect amount of the subject 7 as a testing target is calculated as an estimation value.

The defect amount may be a cross-sectional area of the defect part taken along a plane orthogonal to the axial direction of the subject 7 or a width of the defect part in the axial direction of the subject 7.

(Cross-Sectional Area of Defect Part)

Firstly described is the method using a cross-sectional area of a defect part as the defect amount. In this case, the amplitude of the reflected wave is used in the aforementioned testing method. That is, the data for defect amount estimation is data for cross-sectional area estimation indicating a relationship between a cross-sectional area of a defect part and amplitude of a reflected wave.

Figure 4A:
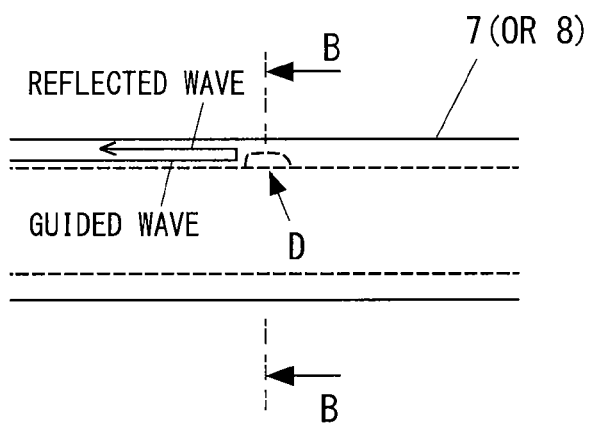
FIG. 4A illustrates a defect part D.
Figure 4B:
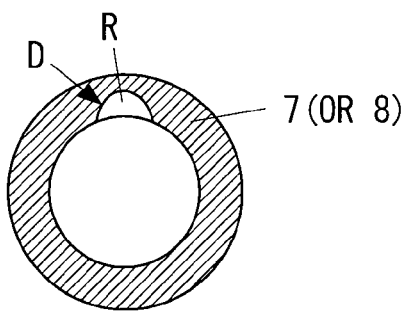
FIG. 4B shows a cross-sectional area of a defect part D.

FIG. 4B shows a cross-sectional area of a defect part D. FIG. 4B is a cross-sectional view taken along the line B-B of FIG. 4A, illustrating a cross section of the subject 7 or 8. The region R in FIG. 4B indicates a cross-sectional area of the defect part D. The cross-sectional area of this defect part D is a cross-sectional area of the defect part D taken along a plane orthogonal to the axial direction of the subject 7 or 8.

Figure 5:
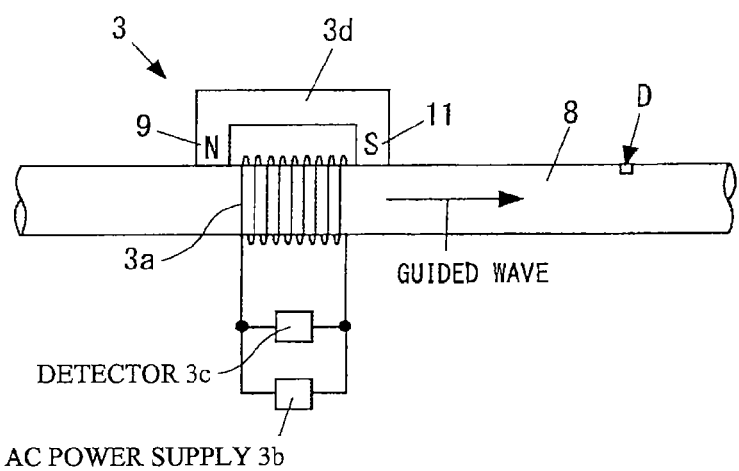
FIG. 5 illustrates the testing device of FIG. 1 attached to a subject as a testing target.

The procedure to obtain the data for cross-sectional area estimation at Step S1 is as follows. Firstly, a subject 8 for testing of the same type (i.e., the same material, dimensions and shape) as the subject 7 as a testing target is prepared, and the testing device 3 is attached to this subject 8 for testing as illustrated in FIG. 5. The way of attaching the testing device 3 is the same as in the above. A part of the subject 8 is cut away using an appropriate tool from the outer periphery face side, whereby a first defect part D is formed at the outer periphery face of the subject 8 as illustrated in FIG. 5. Next, a guided wave at the same frequency and the same amplitude as the guided wave to be generated at Step S2 is generated by the testing device 3 attached to the subject 8 so that the guided wave propagates through the subject 8. A reflected wave of the guided wave reflected from the first defect part D is detected. Such a reflected wave is displayed, as a waveform part like the flaw signal of FIG. 2, on a display of the detector 3c configured to display the waveform as shown in FIG. 2. The amplitude of the reflected wave is recorded and stored in the detector 3c. Next, a new defect part D having a cross-sectional area different from that of the first defect part D is formed in the same manner as in the above. Herein, the subject 8 may be further cut away at the first defect part D to form the new defect part D having a larger cross-sectional area, or the new defect part D may be formed at a different position in the range of the axial direction position of the subject 8 having a substantially same attenuation amount of the reflected wave to be detected. Following the formation of such a new defect part D, a reflected wave of the guided wave reflected from the new defect part D is detected in the same manner, and the amplitude thereof (preferably the maximum value of the amplitude) is recorded. Thereafter still another defect part having a different cross-sectional area is formed in the same manner as in the above, a reflected wave of a guided wave reflected from the defect part D is detected in the same manner as in the above, and the amplitude thereof (preferably the maximum value of the amplitude) is recorded. Such procedure is repeated, whereby data containing the cross-sectional area values (known) of the plurality of (preferably a large number of) defect parts D and a plurality of amplitude values of the reflected waves corresponding to these plurality of (preferably a large number of) cross-sectional area values is acquired. Based on this data, the data for cross-sectional area estimation is obtained.

Figure 6:
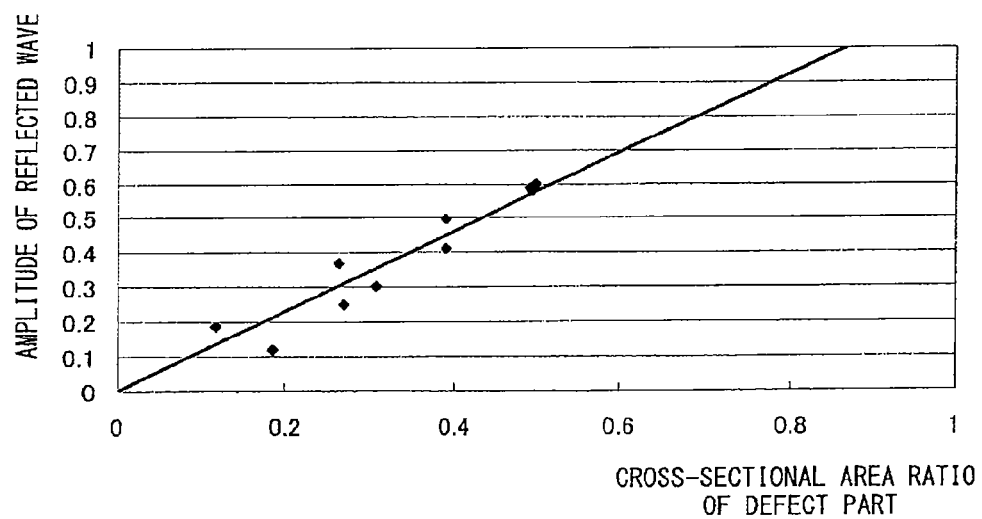
FIG. 6 illustrates a relationship between a cross-sectional area of a defect part and amplitude of a reflected wave.

FIG. 6 illustrates an example of the thus-obtained data for cross-sectional area estimation. In FIG. 6, the horizontal axis represents the magnitude of the cross-sectional area values of the defect parts (in this example, ratios of the cross-sectional area values with reference to a predetermined cross-sectional area value). The vertical axis in FIG. 6 represents the amplitude of reflected waves (in this example, ratios of the amplitude values with reference to a predetermined amplitude value). In FIG. 6, plotted points correspond to the defect parts (and reflected waves from these parts) formed as stated above.

As is understood from FIG. 6, the data for cross-sectional area estimation can be represented approximately proportionally. That is, the data for cross-sectional area estimation can be represented as a half line. Near this half line, the plotted pointes are located, as illustrated in FIG. 6.

The thus-obtained data for cross-sectional area estimation can be used at the above-stated Step S3.

FIG. 5 illustrates the tubular subject 8. In the case of a rod-shaped subject 8, however, a defect part may be formed at an outer periphery part of the subject 8. In this case, a defect amount due to corrosion or the like can be estimated for a subject 7 that is embedded in the ground or a structure.

(Width of Defect Part)

Next, the method using a width of a defect part as the defect amount is described below. In this case, the duration of the reflected wave is used in the aforementioned testing method. That is, the data for defect amount estimation is data for defect width estimation indicating a relationship between a width of a defect part and the duration of a reflected wave.

Figure 7:
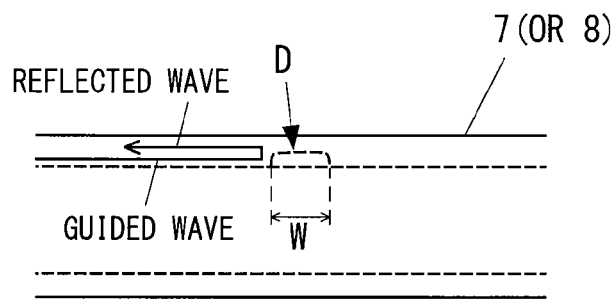
FIG. 7 shows a width of a defect part D.

FIG. 7 shows a width of a defect part D. In FIG. 7, W denotes the width of the defect part D of the subject 7 or 8.

The procedure to obtain the data for defect width estimation at Step S1 is as follows. Firstly, a subject 8 for testing of the same type (i.e., the same material, dimensions and shape) as the subject 7 as a testing target is prepared, and the testing device 3 is attached to this subject 8 for testing as illustrated in FIG. 5. The way of attaching the testing device 3 is the same as in the above. A part of the subject 8 is cut away using an appropriate tool from the outer periphery face side, whereby a first defect part D is formed at the outer periphery face of the subject 8 as illustrated in FIG. 5. Next, a guided wave is generated by the testing device 3 attached to the subject 8, and a reflected wave of the guided wave reflected from the first defect part D is detected. Such a reflected wave is displayed, as a waveform part like the flaw signal of FIG. 2, on a display of the detector 3c configured to display the waveform as shown in FIG. 2. The time duration of the reflected wave detected (e.g., duration T of the flaw signal in FIG. 2) is recorded and stored by the detector 3c. Next, a new defect part D having a width different from that of the first defect part D is formed in the same manner as in the above. Herein, the subject 8 may be further cut away at the first defect part D to form the new defect part D having a larger width, or the new defect part D may be formed at a different position in the range of the axial direction position of the subject 8 having a substantially same attenuation amount of the reflected wave to be detected. Following the formation of such a new defect part D, a reflected wave of the guided wave reflected from the new defect part D is detected, and the duration of the reflected wave is recorded. Thereafter, still another defect part having a different width is formed in the same manner as in the above, a reflected wave of a guided wave reflected from the defect part D is detected in the same manner as in the above, and the duration thereof is recorded. Such procedure is repeated, whereby data containing the width values (known) of the plurality of (preferably a large number of) defect parts D and a plurality of duration values of the reflected waves corresponding to these plurality of (preferably a large number of) width values is acquired. Based on this data, the data for defect width estimation is obtained. Preferably, the plurality of defect parts D have the same cross-sectional area taken along a plane orthogonal to the axial direction of the subject 8.

Figure 8:
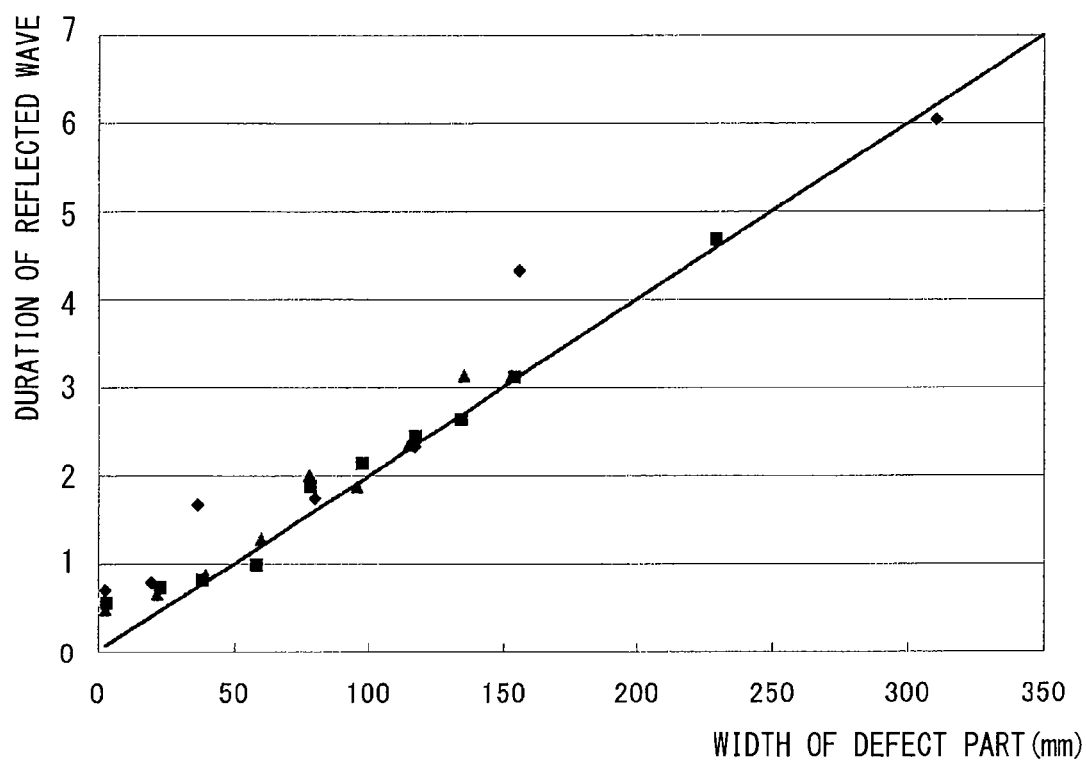
FIG. 8 illustrates a relationship between a width of a defect part and duration of a reflected wave.

FIG. 8 illustrates an example of the thus-obtained data for defect width estimation. In FIG. 8, the horizontal axis represents the width (mm) of the defect parts. The vertical axis in FIG. 8 represents the duration of reflected waves (in this example, ratios of the duration values with reference to a predetermined duration value). In FIG. 8, plotted points correspond to the defect parts (and reflected waves from these parts) formed as stated above.

As is understood from FIG. 8, the data for defect width estimation can be represented approximately proportionally. That is, the data for defect width estimation can be represented as a half line. Near this half line, the plotted pointes are located, as illustrated in FIG. 8.

The thus-obtained data for defect width estimation can be used at the above-stated Step S3.

Since a guided wave suffers less attenuation, when a guided wave is reflected from a defect part within a predetermined range (e.g., within a range of a subject at a distance from the attachment position of the testing device 3 not exceeding 4 to 5 m), such a guided wave and a reflected wave thereof will hardly attenuate in the reciprocating course between the attachment position of the testing device 3 and the reflected position. Therefore, the defect amount (cross-sectional area of the defect part) within the predetermined range can be estimated precisely by the testing method using a guided wave of the present invention.

Meanwhile, in order to estimate a cross-sectional area of a defect part more precisely within such a predetermined range or in order to estimate a cross-sectional area of a defect part outside the predetermined range, attenuation of a reflected wave may be considered. More specifically, a subject for attenuation testing of the same type (i.e., the same material, dimensions and shape) as the subject 7 as a testing target is prepared. Next, defect parts are formed at a plurality of positions in the axial direction of the subject for attenuation testing to have the same cross-sectional area (i.e., cross-sectional area taken along a plane orthogonal to the axial direction of the subject) and the same width (i.e., width in the axial direction of the subject). Thereafter, a guided wave is propagated through the subject for attenuation testing using the aforementioned testing device 3, reflected waves from the respective defect parts are detected, and on the basis of the amplitude values of the reflected waves and the positions of the defect parts in the axial direction, a relationship (called an attenuation relationship) between a distance from the attachment position of the coil 3a or 5a to the reflecting position of the guided waves (i.e., corresponding to the positions of the defect parts in the axial direction) and an attenuation amount or an attenuation ratio (attenuation ratio of the reflected wave with reference to the distance) of the amplitude of the reflected wave is obtained.

In this case, at Step S3, on the basis of the attenuation relationship, the data for cross-sectional area estimation obtained at Step S1, and the amplitude of the reflected wave detected at Step S2, a cross-sectional area of the defect part of the subject 7 as a testing target is estimated with consideration given to the attenuation of the reflected wave. For instance, the amplitude of the reflected wave detected at Step S2 is corrected to the amplitude to be free from the attenuation on the basis of the reflecting position of the reflected wave and the attenuation relationship, and this corrected amplitude is applied to the data for cross-sectional area estimation, whereby a cross-sectional area of the defect part of the subject 7 can be estimated. In this case, for example, a plurality of defect parts having different cross-sectional areas may be formed at the same position, and the data for cross-sectional area estimation without attenuation in the reflected wave may be obtained at Step S1 on the basis of the position of the defect parts, the position of the coil 3a, the amplitude of the reflected wave and the attenuation relationship.

The data for defect amount estimation may be stored in the aforementioned detector 3c. Then, at Step S3, the detector 3c may recognize the amplitude or duration of the reflected wave, and may estimate a value of the defect amount (the aforementioned cross-sectional area or the aforementioned width of the defect part) of the subject 7 on the basis of the magnitude (the amplitude or duration of the reflected wave) and the data for defect amount estimation. Alternatively, at Step S3, the display provided in the detector 3c may display the reflected wave detected at Step S2 as illustrated in FIG. 2, a person viewing this display may measure and recognize the amplitude or duration of the reflected wave, and the defect amount of the subject 7 may be estimated on the basis of the amplitude or duration of the reflected wave and the data for defect amount estimation.

Preferably, the testing device 3 used at Step S1 to obtain the data for defect amount estimation and the testing device 3 used at Step S2 are the same. Thereby, estimation precision of the defect amount can be kept high.

Embodiment 2

Figure 9:
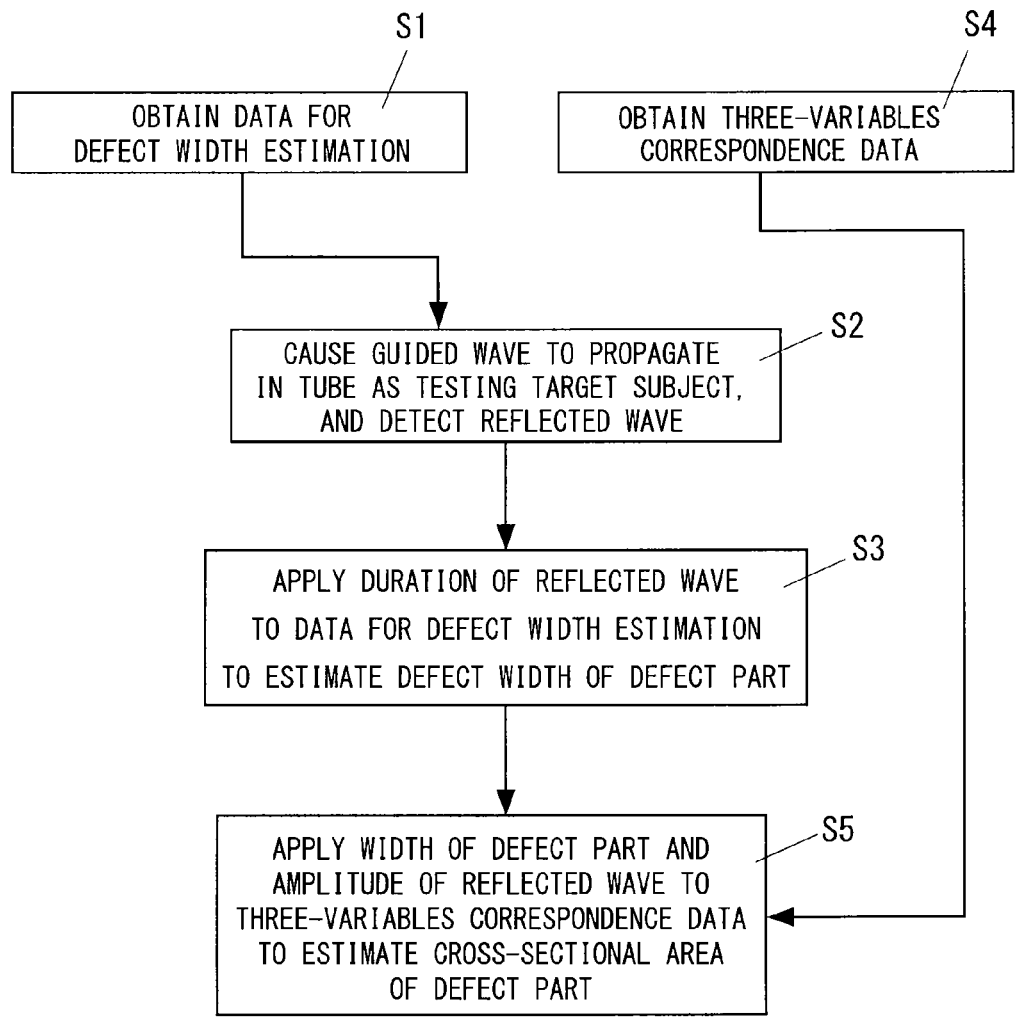
FIG. 9 is a flowchart illustrating a testing method using a guided wave according to Embodiment 2 of the present invention.

FIG. 9 shows a testing method using a guided wave according to Embodiment 2 of the present invention. Embodiment 2 may be the same as Embodiment 1 other than the points described below.

When a width of a defect part is estimated at the aforementioned Step S3, a cross-sectional area of the defect part may be estimated by the testing method of FIG. 9.

In the testing method of FIG. 9, Steps S1, S2 and S3 are the same as the aforementioned Steps S1, S2 and S3 except that the data for the defect width estimation is obtained at Step S1. The testing method of FIG. 9 further includes Steps S4 and S5.

At Step S4, a three-variables correspondence data to be used at Step S5 is obtained.

The three-variables correspondence data indicates a relationship among the amplitude of a reflected wave, a width of a defect part and a cross-sectional area of the defect part.

Figure 10:
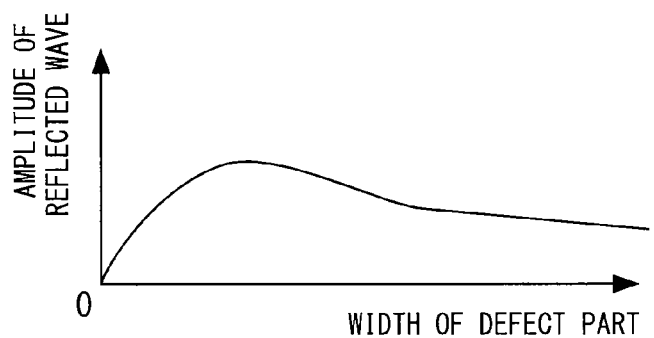
FIG. 10 illustrates a relationship between a width of a defect part D and amplitude of a reflected wave.

The three-variables correspondence data is described below. When defect parts have a constant cross-sectional area, the amplitude of the reflected wave as stated above detected by the testing device 3 varies with a width of the defect parts as illustrated in FIG. 10. Considering this variation, a cross-sectional area of a defect part can be found more precisely. When defect parts have a constant width, the amplitude of the reflected wave will vary with a cross-sectional area of the defect parts as illustrated in FIG. 6. Therefore, the three-variables correspondence data can be represented in a three-dimensional rectangular coordinates system, each axis of which represents the amplitude of a reflected wave, the width of a defect part and a cross-sectional area of the defect part, with a curved face formed by a trail of the points on the curve of FIG. 10 so as to be depicted proportionally to the cross-sectional area of the defect parts as shown in FIG. 6.

A method to obtain the three-variables correspondence data is as follows. A subject 8 for testing of the same type as the subject 7 as a testing target is prepared, a guided wave is propagated through the subject 8 for testing and a reflected wave from a defect part is detected. Thereby, on the basis of the widths and the cross-sectional areas of a plurality of defect parts and the amplitude values of the reflected waves corresponding to the plurality of defect parts, the three-variables correspondence data is obtained.

More specifically, a subject 8 for testing of the same type (i.e., the same material, dimensions and shape) as the subject 7 as a testing target is prepared, and the testing device 3 is attached to this subject 8 for testing as stated above. A part of the subject 8 is cut away using an appropriate tool from the outer periphery face side, whereby a first defect part D is formed at the outer periphery face of the subject 8 as illustrated in FIG. 5. Next, a guided wave is generated by the testing device 3 attached to the subject 8, and a reflected wave of the guided wave reflected from the first defect part D is detected. Such a reflected wave is displayed, as a waveform part as in the flaw signal of FIG. 2, on a display of the detector 3c configured to display the waveform as shown in FIG. 2. The amplitude of the reflected wave is recorded and stored in the detector 3c. Next, a new defect part D having at least one of a width (width of the subject 8 in the axial direction) and a cross-sectional area (cross-sectional area taken along a plane orthogonal to the axial direction of the subject 8) different from those of the first defect part D is formed in the same manner as in the above. Herein, the subject 8 may be further cut away at the first defect part D to form the new defect part D having a larger width, or the new defect part D having at least one of a different width and a different cross-sectional area may be formed at a different position in the range of the axial direction position of the subject having a substantially same attenuation amount of the reflected wave to be detected. Following the formation of such a new defect part D, a reflected wave of the guided wave reflected from the new defect part D is detected in the same manner, and the amplitude thereof is recorded. Thereafter still another defect part having at least one of a different width and a different cross-sectional area is formed in the same manner as in the above, a reflected wave of a guided wave reflected from the defect part D is detected in the same manner as in the above, and the amplitude thereof is recorded. Such procedure is repeated, whereby a plurality of sets (preferably a large number of sets) of data containing the width values (known) of the defect parts D, the cross-sectional area values (known) of the defect parts D and amplitude values of the reflected waves corresponding to the defect parts D is acquired. Based on this plurality of sets of data, the three-variables correspondence data is obtained.

At Step S5, on the basis of the width of the defect part estimated at Step S3, the amplitude of the reflected wave detected at Step S2 and the three-variables correspondence data obtained at Step S4, a cross-sectional area of the defect part is found.

At Step S5, on the basis of the aforementioned attenuation relationship, the width of the defect part estimated at Step S3, the amplitude of the guided wave detected at Step S2 and the three-variables correspondence data obtained at Step S4, a cross-sectional area of the defect part of the subject 7 as a testing target may be estimated by taking into consideration attenuation of the reflected wave. For instance, on the basis of the reflecting position of the reflected wave and the attenuation relationship, the amplitude of the reflected wave detected at Step S2 may be corrected to the amplitude to be free from attenuation, and this corrected amplitude is applied to the three-variables correspondence data, whereby a cross-sectional area of the defect part of the subject 7 can be estimated. In this case, for example, a plurality of defect parts having at least one of different widths and different cross-sectional areas may be formed at the same position, and the three-variables correspondence data without attenuation in the reflected wave may be obtained at Step S4 on the basis of the cross-sectional areas and the widths of the plurality of defect parts, the position of the defect parts, the position of the coil 3a, the amplitude of the reflected wave and the attenuation relationship.

Such three-variables correspondence data may be stored at the aforementioned detector 3c. Then, at Step S5, the detector 3c may recognize the amplitude of the reflected wave detected at Step S2, and may estimate a value of the cross-sectional area of the subject 7 on the basis of the amplitude, the width of the defect part estimated at Step S3 and the three-variables correspondence data obtained at Step S4. Alternatively, at Step S5, the display provided in the detector 3c may display the reflected wave detected at Step S2 as illustrated in FIG. 2, a person viewing this display may measure and recognize the amplitude of the reflected wave, and the cross-sectional area of the subject 7 may be estimated on the basis of the amplitude, the width of the defect part estimated at Step S3 and the three-variables correspondence data obtained at Step S4.

Preferably, the testing device 3 used at Step S4 to obtain the three-variables correspondence data and the testing device 3 used at Step S2 are the same. Thereby, estimation precision of the cross-sectional area can be kept high.

The present invention is not limited to the aforementioned embodiments and can be variously modified without departing from the scope of the present invention.

For instance, when the subject has a rod shape, a defect part will be located mainly on an outer periphery face of the subject. On the other hand, when the subject has a tubular shape, a defect part may be on an inner periphery face or on an outer periphery face of the subject. Accordingly in order to obtain the data for defect amount estimation or the three-variables correspondence data, a defect part may be formed on the outer periphery surface or on the inner periphery surface of the subject 8 for testing. In the aforementioned embodiments, the subject 8 is cut away from the outer periphery face side, whereby a plurality of defect parts are formed on the outer periphery face of the subject 8 for testing, and the data for defect amount estimation or the three-variables correspondence data is obtained on the basis of reflected waves from these defect parts. The thus-obtained data for defect amount estimation or three-variables correspondence data is applicable precisely to the case of estimating the magnitude of a defect part on the inner periphery face of the subject 7 as a testing target as well. That is, the data for defect amount estimation or the three-variables correspondence data obtained using defect parts formed on the outer periphery face of the subject 8 for testing is almost equal to the data for defect amount estimation or the three-variables correspondence data obtained using defect parts formed on the inner periphery face of the subject 8 for testing. Accordingly, the data for defect amount estimation or the three-variables correspondence data may be obtained using defect parts formed on the outer periphery face of the subject 8 for testing or using defect parts formed on the inner periphery face of the subject 8 for testing. Herein, defect parts can be more easily formed on the outer periphery face.

Figure 11:
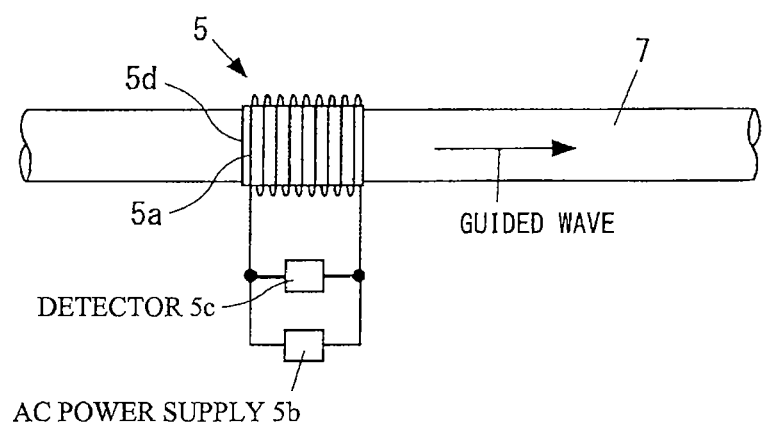
FIG. 11 illustrates another exemplary configuration of a testing device that can be used for a testing method using a guided wave according to the present invention.

Although the aforementioned embodiments use the testing device 3 using an L-mode guided wave, a testing device using another mode may be used. For instance, a testing device 5 using a T-mode guided wave may be used as illustrated in FIG. 11. The testing device 5 of FIG. 11 includes a ferromagnetic metal plate 5d, a coil 5a, an AC power supply 5b and a detector 5c. The ferromagnetic metal plate 5d is a metal plate made of a ferromagnetic material, and the ferromagnetic metal plate 5d is directly wound around an outer periphery face of the subject 7. The coil 5a is wound on the ferromagnetic metal plate 5d around the subject 7. The detector 5c is connected to the coil 5a for detection of a voltage between both ends of the coil 5a. Attaching the ferromagnetic metal plate 5d, the coil 5a and the detector 5c in this way, when AC current is passed through the coil 5a from the AC power supply 5b, a T-mode guided wave is generated in the subject 7, and the guided wave propagates along the longitudinal direction of the subject 7. Such a propagating guided wave is reflected at a defect part such as a flaw or corrosion (wastage) of the subject 7, and returns to the coil 5a side by propagation. The detector 5c detects a voltage generated between both ends of the coil 5a as the reflected wave reaches the part of the coil 5a.

The configuration of the testing device 3, 5 is not limited to the exemplary configurations illustrated in FIG. 1 and FIG. 11.

A plurality of defect parts D having different cross-sectional areas and widths are formed in the subject 8 for testing at different known positions in the axial direction. In this state, a guided wave is generated by a testing device attached to the subject 8 at a known position, reflected waves from the defect parts D are detected, and on the basis of the amplitude of reflected waves, the duration, and the plurality of known cross-sectional areas and widths, the data for defect amount estimation or the three-variables correspondence data may be obtained.

When a defect part has a width larger than the length of a guided wave (e.g., the two wavelengths in the case of a guided wave generated having the length of two wavelengths), the present invention may be embodied by setting the duration from the timing when the reflected wave corresponding to a starting point of the defect part at a near side of the attachment position of the testing device is detected to the timing when the reflected wave corresponding to an ending point of the defect part at a far side of the attachment position of the testing device is detected.

Although not illustrated and described, each testing device may be provided with a cancellation device configured to intensify the amplitude of the guided wave propagating in one of two opposed axial directions of the subject and cancel the guided wave in the other axial direction. Similarly to the testing devices, such a cancellation device includes a coil and an AC power supply, and the coil is wound around the subject at a position away from the coil of the testing device by ¼ of the wavelength of the guided wave, and the coil of the cancellation device generates a guided wave out of phase by ¼ of the cycle of the guided wave generated by the coil of the testing device. Such a cancellation device allows a guided wave to propagate in one axial direction only.

DESCRIPTION OF REFERENCE NUMERALS

3: Testing device, 3a: Coil, 3b: AC power supply
3c: Detector, 3d: Magnet, 5: Testing device
5a: Coil, 5b: AC power supply, 5c: Detector
5d: Ferromagnetic metal plate, 7: Subject as a testing target
8: Subject for testing, 9: North pole, 11: South pole

The invention claimed is:

1. A testing method using a guided wave, of generating a guided wave to propagate through a subject as a testing target in a longitudinal direction of the subject, detecting a reflected wave of the guided wave and examining the subject on a basis of the reflected wave, comprising the steps of:
   (A) obtaining data for defect amount estimation beforehand indicating a relationship between a width of a defect part in a longitudinal direction of a subject and duration of a reflected wave;
   (B) generating a guided wave so as to propagate through the subject, and detecting a reflected wave of the generated guided wave;
   (C) estimating a width of a defect part in the longitudinal direction of the subject on based on the data for defect amount estimation obtained in step (A) and duration of the reflected wave detected in step (B);
   (D) obtaining three-variables correspondence data beforehand indicating a relationship among amplitude of a reflected wave, a width of a defect part in the longitudinal direction of the subject and a cross-sectional area of the defect part taken along a plane orthogonal to the longitudinal direction of the subject; and
   (E) estimating a cross-sectional area of the defect part taken along a plane orthogonal to the longitudinal direction of the subject based on the width of the defect part in the longitudinal direction of the subject estimated in step (C), and the amplitude of the reflected wave detected in step (B) and the three-variables correspondence data obtained in step (D).

2. The testing method using a guided wave according to claim 1, wherein
   in (A), a subject for testing of a same type as the subject as a testing target is prepared, a guided wave is propagated through the subject for testing and a reflected wave thereof at a defect part is detected, whereby on a basis of a width of each of a plurality of defect parts in the longitudinal direction of the subject and duration of the reflected waves corresponding to the plurality of defect parts, the data for defect amount estimation is obtained.

3. The testing method using a guided wave according to claim 1, wherein
   in (D), a subject for testing of a same type as the subject as a testing target is prepared, a guided wave is propagated through the subject for testing and a reflected wave thereof at a defect part is detected, whereby on a basis of a width of each of a plurality of defect parts in the longitudinal direction of the subject, a cross-sectional area of each of the plurality of defect parts taken along a plane orthogonal to the longitudinal direction of the subject and amplitude of the reflected waves corresponding to the plurality of defect parts, the three-variables correspondence data is obtained.

4. The testing method using a guided wave according to claim 2, wherein
   in (D), a subject for testing of a same type as the subject as a testing target is prepared, a guided wave is propagated through the subject for testing and a reflected wave thereof at a defect part is detected, whereby on a basis of a width of each of a plurality of defect parts in the longitudinal direction of the subject, a cross-sectional area of each of the plurality of defect parts taken along a plane orthogonal to the longitudinal direction of the subject and amplitude of the reflected waves corresponding to the plurality of defect parts, the three-variables correspondence data is obtained.

\* \* \* \* \*